United States Patent [19]

Boireau et al.

[11] Patent Number: 5,674,885
[45] Date of Patent: Oct. 7, 1997

[54] APPLICATION OF RILUZOLE IN THE TREATMENT OF PARKINSON'S DISEASE AND PARKINSONIAN SYNDROMES

[75] Inventors: Alain Boireau, Sucy en Brie; Adam Doble, Paris; Pierre Dubedat, Nogent Sur Marne; Erik Louvel, Paris; Mireille Meunier, Dourdan; Jean-Marie Miquet, Orsay; Jean-Marie Stutzmann, Villecresnes, all of France

[73] Assignee: Rhone-Poulenc Rorer S.A., Antony, France

[21] Appl. No.: 446,734

[22] PCT Filed: Jan. 3, 1994

[86] PCT No.: PCT/FR94/00003

§ 371 Date: Jun. 6, 1995

§ 102(e) Date: Jun. 6, 1995

[87] PCT Pub. No.: WO94/15601

PCT Pub. Date: Jul. 21, 1994

[30] Foreign Application Priority Data

Jan. 7, 1993 [FR] France ................. 93 00074

[51] Int. Cl.$^6$ ........................ A61K 31/425
[52] U.S. Cl. ........................ 514/367
[58] Field of Search ................ 514/367

[56] References Cited

U.S. PATENT DOCUMENTS 4,370,338  1/1983  Mizoule .................. 424/270

FOREIGN PATENT DOCUMENTS 0 050 551  4/1982  European Pat. Off. .
0 517 347  12/1992  European Pat. Off. .

OTHER PUBLICATIONS

The Journal of Neuroscience, vol. 9, No. 11, 1989, pp. 3720–3727 C. Malgouris et al.
The Japanese Journal of Pharmacology, vol. 9, No. Supl, 1989, p. 8P J.C. Blanchard et al.
Neuroscience Letters, vol. 140, No. 2, 1992, pp. 225–230, J. Pratt et al.
Neuropharmacology, vol. 24, No. 11, 1985, J. Benavides et al.
Neuroscience Letters, vol. 147, No. 2, 1992, pp. 209–212, A. Cheramy et al.
Trends in Neurosciences, vol. 12, No. 8, 1989, pp. 285–286, Klockgether.
Patricia K. Sonsalla et al., "MK–801 Falls to Protect Against the Dopaminergic Neuropathology Produced by Systemic 1–Methyl–4–Phenyl–1,2,3,6–Tetrahydropyridine in Mice or Intranigral–1–Methyl–4–Phenylpyridinium in Rats" Journal of Neurochemistry, vol. 58, No. 5, 1992, pp. 1979–1982.
Andreas Kupsch et al., "Do NMDA receptor Antagonists Protect Against MPTP–Toxicity? Biochemical and immunocytochemical Analyses in Black Mice", Brain Research, 592, (1992), pp. 74–83.
R. Gill et al., "Systemic Administration of MK–801 Protects Against Ischemia–Induced Hippocampal Neuro–degeneration in the Gerbil", The Journal of Neuroscience, Oct. 1987, pp. 3343–3349.
P. A. Loschmann et al., "Synergism of the AMPA–antagonist NBQX and the NMDA–antagonists CPP with L–Dopa in Models of Parkinson's Disease, Journal of Neural Transmission" (1991), pp. 203–213.
Malcolm J. Sheardown et al., "2,3–Dihydroxy–6–nitro–7–sulfamoyl–benzo(F)quinoxaline: A Neuroprotectant for Cerebral ischemia", Science, vol. 247, pp. 571–574, 1990.
M. Rosario Luquin et al., "The AMPA Receptor Antagonist NBQX Does Not Alter the Motor Response Induced by Selective Dopamine Agonists in MPTP–treated Monkeys", European Journal of Pharmacology, (1993), pp. 297–300.
D. Sauer et al., "The Competitive NMDA Receptor Antagonist CGP 40116 is a Potent Neuroprotectant in a Rat Model of Focal Cerebral Ischemia", J. Neural Trasm (1994), pp. 81–89.
Carolina M. Maier et al., "Neuroprotection by the N–Methyl–D–Aspartate Receptor Antagonist CGP 40116: In Vivo and In Vitro Studies", Journal of Neurochemistry, vol. 65, No. 2, 1995, pp. 652–659.
Close et al., *Psychopharmacology* 102:295–300 (1990).
Turski et al., *Nature* 349, pp. 414–418 (1991).
Wüllner, *Pharmacology*, 31, 7:713–715 (1992).

Primary Examiner—William R.A. Jarvis
Attorney, Agent, or Firm—Finnegan, Henderson, Farabow, Garrett & Dunner, L.L.P.

[57] ABSTRACT

This invention relates to an application of riluzole or the pharmaceutically acceptable salts in the preparation of drugs for the treatment of Parkinson's disease and parkinsonian syndromes.

2 Claims, No Drawings

APPLICATION OF RILUZOLE IN THE TREATMENT OF PARKINSON'S DISEASE AND PARKINSONIAN SYNDROMES

FIELD OF THE INVENTION

This application claims priority to PCT/FR94/00003 filed Jan. 3, 1994.

The present invention relates to a novel therapeutic application of riluzole (6-trifluoromethoxy-2-aminobenzothiazole) or the pharmaceutically acceptable salts of this compound.

BACKGROUND OF THE INVENTION

Riluzole is useful as an anticonvulsant, anxiolytic and hypnotic medicinal product (Patent EP 50,551), in the treatment of schizophrenia (EP 305,276), in the treatment of sleep disorders and depression (EP 305,277), in the treatment of cerebrovascular disorders and as an anaesthetic (EP 282,971).

DESCRIPTION OF THE INVENTION

It has now been found, surprisingly, that this compound may also be used in the treatment of Parkinson's disease and parkinsonian syndromes.

The neurotoxin MPTP (1-methyl-4-phenyl-1,2,3,6-tetrahydropyridine) is known to induce a syndrome similar to Parkinson's disease. This syndrome results from a degeneration of the dopaminergic nigrostriatal neurons in primates (R. S. Burns et al., Proc. Natl. Acad. Sci., 80, 4546–4550 (1983)), in man (J. W. Langston et al., Science, 219, 979–980 (1983)) and in mice (R. E. Heikkila et al., Science, 224, 1451–1453 (1984)).

EXAMPLES

The activity of riluzole was hence demonstrated in mice by measuring MPTP-induced decreases in the striatal and cortical dopamine levels in comparison with those of control animals.

Mice (C57BL/6) weighing 20–25 g are injected intraperitoneally 3 times at 2-hour intervals with 15 mg/kg of MPTP. Thirty minutes before the first injection of MPTP, and then 2 hours 30 minutes, 5 hours 30 minutes and 7 hours 30 minutes after the first injection of MPTP, from 1 to 40 mg/kg of the product under study, depending on the product, are administered. Over the next 3 days, from 1 to 40 mg/kg of the product under study, depending on the product, are administered twice daily. The mice are sacrificed 8 days after injection of MPTP. The striatum and the frontal cortex are dissected and stored at −70° C. until the time of their analysis. Dopamine levels are measured by high pressure liquid chromatography with electrochemical detection. Statistical analyses are performed using ANOVA followed by Scheffé's test.

The results obtained are recorded in the following table:

|  | dopamine level pmol/mg in the striatum (% relative to controls) | dopamine level pmol/mg in the frontal cortex (% relative to controls) |
|---|---|---|
| controls | 876 ± 64 | 2.486 ± 0.290 |
| animals receiving only MPTP | 219 ± 18 (−75%) | 1.481 ± 0.180 (−40%) |
| animals treated with riluzole | 378 ± 39 (−57%) | 2.359 ± 0.185 (−5%) |

As pharmaceutically acceptable salts, the addition salts with inorganic acids, such as hydrochloride, sulphate, nitrate or phosphate, or organic acids, such as acetate, propionate, succinate, oxalate, benzoate, fumarate, maleate, methanesulphonate, isethionate, theophyllineacetate, salicylate, phenolphthalinate or methylenebis(β-hydroxynaphthoate), or substitution derivatives of these derivatives, may be mentioned in particular.

The medicinal products consist at least of riluzole, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally or parenterally.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colouring, a coating (dragés) or a vanish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can comprise substances other than diluents, for example wetting, sweetening, thickening, flavouring or stabilizing products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporation of sterilizing agents in the composition, by irradiation or by heating. They may also be prepared in the form of sterile solid compositions which can be dissolved at the time of use in sterile water or any other sterile injectable medium.

The doses depend on the effect sought, the treatment period and the administration route used; they are generally between 50 and 400 mg per day via the oral route for an adult, with single doses ranging from 25 to 200 mg of active substance.

Generally speaking, the doctor will determine the appropriate dosage in accordance with the age, the weight and all other factors specific to the subject to be treated.

The examples which follow illustrate medicinal products according to the invention:

Example A

Tablets containing a 50 mg dose of active product and having the following composition are prepared according to the usual technique:

| | |
|---|---|
| Riluzole | 50 mg |
| Mannitol | 64 mg |
| Microcrystalline cellulose | 50 mg |
| Povidone excipient | 12 mg |
| Sodium carboxymethylstarch | 16 mg |
| Talc | 4 mg |
| Magnesium stearate | 2 mg |
| Colloidal silica, anhydrous | 2 mg |
| Mixture of methylhydroxypropyl-cellulose, polyethylene glycol 6000 and titanium dioxide (72:3.5: 24.5) q.s. 1 finished film-coated tablet weighing 245 mg | |

Example B

Hard gelatin capsules containing a 50 mg dose of active product and having the following composition are prepared according to the usual technique:

| | |
|---|---|
| Riluzole | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

Example C

An injection containing 10 mg of active product and having the following composition is prepared:

| | |
|---|---|
| Riluzole | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water | q.s. 4 cm$^3$ |

The invention also relates to the process for preparing medicinal products which can be used in the treatment of Parkinson's disease and parkinsonian syndromes, consisting in mixing riluzole or the pharmaceutically acceptable salts of this compound with one or more compatible and pharmaceutically acceptable diluents and/or adjuvants.

The invention also relates to a method for treating a mammal, and in particular man, having Parkinson's disease or parkinsonian syndromes, comprising the administration of an effective amount of riluzole or the pharmaceutically acceptable salts of this compound.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Method for the treatment of Parkinson's disease and/or a parkinsonian syndrome comprising treating a patient in recognized need of such treatment with an effective amount of riluzole or a pharmaceutically acceptable salt thereof.

2. A method according to claim 1, wherein said effective amount is 50 to 400 mg of riluzole daily.

* * * * *